United States Patent [19]

Sears

[11] Patent Number: 5,441,519
[45] Date of Patent: Aug. 15, 1995

[54] IMPLANTABLE ATRIAL DEFIBRILLATOR HAVING DELAYED INTERVENTION THERAPY

[75] Inventor: Gena K. Sears, Seattle, Wash.

[73] Assignee: InControl, Inc., Redmond, Wash.

[21] Appl. No.: 383,894

[22] Filed: Feb. 6, 1995

[51] Int. Cl.$^6$ .............................................. A61N 1/39
[52] U.S. Cl. ...................................................... 607/5
[58] Field of Search .................................. 607/4, 5, 14

[56] References Cited

U.S. PATENT DOCUMENTS 5,366,486  11/1994  Zipes et al. ............................. 607/5
5,403,354   4/1995  Adams et al. ........................... 607/5

Primary Examiner—William E. Kamm
Assistant Examiner—Scott M. Getzow
Attorney, Agent, or Firm—Richard O. Gray, Jr.

[57] ABSTRACT

An implantable atrial defibrillator delays therapy intervention for a delay time period after initial detection of fibrillation to provide the atria with an opportunity to spontaneously revert to normal sinus rhythm before cardioversion is attempted. A timer times the delay time period responsive to the first initial detection of fibrillation by a fibrillation detector. After timer time-out, the fibrillation detector redetects for atrial fibrillation. If the atria are still in fibrillation, a cardiovertor cardioverts the atria. If the atria are not in fibrillation, cardioverting therapy is withheld.

7 Claims, 2 Drawing Sheets

IMPLANTABLE ATRIAL DEFIBRILLATOR HAVING DELAYED INTERVENTION THERAPY

BACKGROUND OF THE INVENTION

The present invention generally relates to an automatic implantable atrial defibrillator for delivering cardioverting or defibrillating electrical energy to the atria of a human heart. The present invention is more particularly directed to such an atrial defibrillator which delays therapy intervention for a delay period once atrial fibrillation is originally detected to provide the heart with an opportunity to self-revert to normal sinus rhythm before cardioverting electrical energy is applied to the atria to cardiovert the heart.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Implantable atrial defibrillators proposed in the past have exhibited a number of disadvantages which probably has been the cause of these defibrillators from becoming a commercial reality. Two such defibrillators, although represented as being implantable, were not fully automatic, requiring human interaction for cardioverting the heart. Both of these defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

Implantable ventricular defibrillators for applying defibrillating electrical energy to the ventricles of the heart are well known and have been commercially available for a number of years. Ventricular fibrillation is life threatening, resulting in unconsciousness in just a few seconds and leading to death in just a few minutes. Hence, implantable ventricular defibrillators must be fully automatic for detecting ventricular fibrillation and quickly, without delay, providing defibrillating therapy to the ventricles when ventricular fibrillation is detected. The amount of energy required to cardiovert or defibrillate the ventricles with implantable devices has been on the order of ten joules or more. At such energies, cardioversion can be extremely painful and traumatic. Fortunately, or unfortunately, when patients are being cardioverted for ventricular fibrillation, they are generally already unconscious.

Episodes of atrial fibrillation occur much more frequently than do episodes of ventricular fibrillation, and patients do not normally lose consciousness as a result of their atrial fibrillation. Even though the energies required to cardiovert or defibrillate the atria have been reduced to a few joules or less, cardioversion even at these energy levels can be perceived by patients as being painful, or at least causing discomfort. Hence, any reduction in the number of required cardioversions of a patient would be considered desirable.

The present invention addresses the issue of decreasing the number of required atrial cardioversions by an implantable atrial defibrillator. This not only serves to obviate unrequired cardioversion to limit patient discomfort, but additionally serves to lengthen the useful life of an atrial defibrillator by conserving energy. The atrial defibrillator of the present invention achieves these goals by taking advantage of the fact that in some atrial fibrillation patients, some of their atrial fibrillation episodes will spontaneously revert to normal sinus rhythm within some reasonable time period from initial episode onset. In these cases, although immediate cardioversion would most likely be successful, such immediate intervention or therapy would also have been unnecessary. Hence, the number of cardioversion attempts can be reduced without compromising the patient as long as the atrial fibrillation episodes are not permitted to persist too long.

SUMMARY OF THE INVENTION

The present invention provides an implantable atrial defibrillator for applying cardioverting electrical energy to the atria of a human heart in need of cardioversion. The atrial defibrillator includes sensing means for sensing electrical activity of the heart, atrial fibrillation detecting means responsive to the sensed electrical activity of the heart for detecting if the heart is in atrial fibrillation and providing a first detect signal upon detecting atrial fibrillation, and timing means for timing a delay time period responsive to the first detect signal and providing a time-out signal upon timing the delay time period. The atrial fibrillation detection means is further responsive to the time-out signal for redetecting for atrial fibrillation of the heart and provides a second detect signal upon redetecting atrial fibrillation. Cardioverting means, responsive to the second detect signal provided by the atrial fibrillation detecting means, applies cardioverting electrical energy to the atria of the heart.

The present invention further provides a method of applying cardioverting electrical energy to the atria of a human heart in need of cardioversion. The method includes the steps of sensing electrical activity of the heart, detecting if the heart is in atrial fibrillation in response to the sensed electrical activity, and timing a delay time period upon detecting atrial fibrillation of the heart. The method includes the further steps of redetecting for atrial fibrillation of the heart after the delay time period is completed and responsive to the sensed electrical activity, and applying cardioverting electrical energy to the atria upon redetecting atrial fibrillation of the heart.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
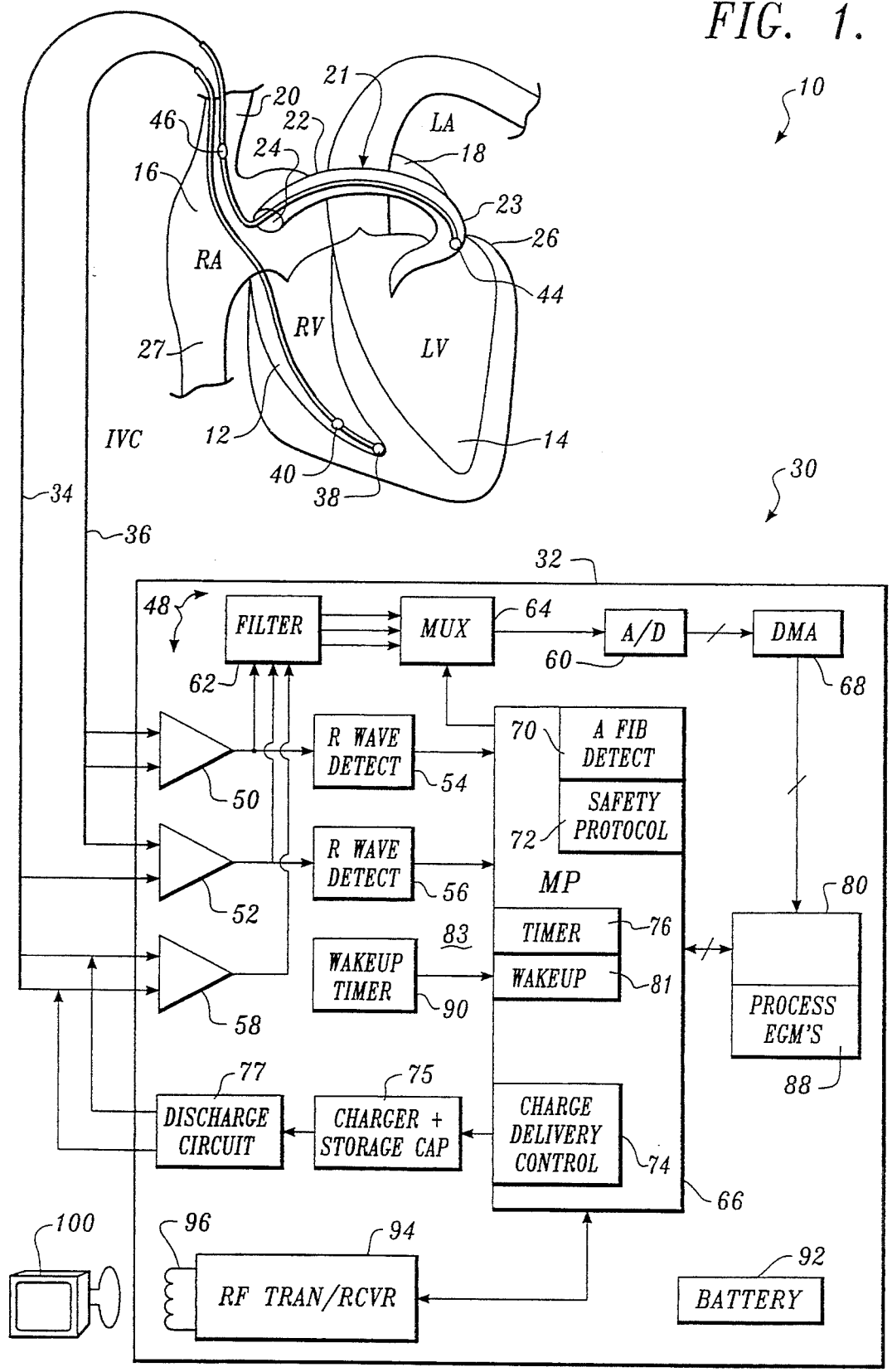
FIG. 1 is a schematic block diagram of a fully implantable atrial defibrillator embodying the present invention.

Referring now to FIG. 1, it illustrates an implantable automatic atrial defibrillator 30 embodying the present invention.

The atrial defibrillator 30 includes an implantable enclosure 32 and an implantable lead system including an intravascular lead 34 and an endocardial lead 36. The endocardial lead 36 has tip and ring electrodes 38 and 40 respectively adapted for placement in the right ventricle 12. The intravascular lead 34 has a tip electrode 44 adapted for placement in the coronary sinus 22 or the great cardiac vein 23 and a ring electrode 46 adapted for placement in the superior vena cava 20 or right atrium 16. An alternative lead system may include separate leads for electrodes 44 and 46. This requires an additional endocardial lead (not shown in FIG. 1) adapted for placing electrode 46 in the superior vena cava 20 or the right atrium 16.

Electrodes 44 and 46 of lead 34 sense atrial activity of the heart. Electrodes 44 and 46 perform the additional function of applying cardioverting electrical energy across the atria 16 and 18 of the heart.

Electrodes 38 and 40 sense R waves of the heart and may be referred to herein as the first electrode pair. Electrode 44 together with either electrode 38 or electrode 40 also sense R waves of the heart and may be referred to herein as the second electrode pair. The dual sensing of the R waves between the first and second electrode pairs is performed for the purpose of reliably sensing the R waves as fully described in U.S. Pat. No. 5,348,021, which issued on Sep. 20, 1994, for "APPARATUS AND METHOD FOR RELIABLY DETECTING A DEPOLARIZATION ACTIVATION WAVE OF THE HEART AND ATRIAL DEFIBRILLATOR UTILIZING SAME", which is assigned to the assigned of the present invention and incorporated herein by reference.

The implantable enclosure 32 includes a microprocessor 66 and a memory 80. The microprocessor controls the overall function of the atrial defibrillator 30 under software controlled by operating instructions stored in a memory 80. The memory 80 includes a process memory portion 88 for storing electrocardiogram data samples to be processed by the microprocessor 66 as will be described subsequently.

Within the enclosure 32, the atrial defibrillator 30 further includes a data acquisition means 48 including sense amplifiers 50, 52, and 58, filter 62, multiplexer 64, analog-to-digital converter 60, direct memory access controller 68, and memory 80. Sense amplifier 50 is coupled to electrodes 38 and 40 of lead 36 and sense amplifier 52 is coupled to electrode 44 of lead 34 and to either electrode 38 or electrode 40 of lead 36. The sense amplifiers 50 and 52 amplify the electrogram signals provided by the first and second pairs of electrodes respectively and provide R wave detectors 54 and 56 respectively with an amplified output. The R wave detectors 54 and 56 each include a threshold circuit which isolates the R waves from the amplified electrograms provided by sense amplifiers 50 and 52. The outputs of the R wave detectors 54 and 56 are coupled to the microprocessor for conveying the isolated R waves to the microprocessor 66.

Sense amplifier 58 is coupled to electrodes 44 and 46 of lead 34. The sense amplifier 58 provides an amplified output of the electrograms sensed by the first electrode pair consisting of electrodes 44 and 46. The electrograms provided by sense amplifier 58 predominantly represent atrial activity of the heart 10.

The outputs of the sense amplifiers 50, 52 and 58 are coupled to an analog-to-digital converter 60 through the filter 62 and the multiplexer 64. The analog-to-digital converter 60 digitizes the electrograms provided by the amplifiers 50, 52 and 58 to generate electrogram digital data samples. The electrogram samples are conveyed to the direct memory access 68 which then stores the electrogram samples in memory portion 88 of memory 80.

In controlling the function of the atrial defibrillator 30, the microprocessor 66 implements an atrial fibrillation detection algorithm represented by an atrial fibrillation detector 70. When the atrial fibrillation detector 70 is to determine if the heart 10 is in atrial fibrillation, eight seconds of electrogram digital data from amplifiers 50 and 58 are stored in memory portion 88. The microprocessor then accesses that data when implementing the atrial fibrillation detector 70 to determine if the atria are in fibrillation. The atrial fibrillation detector may be implemented as disclosed in copending U.S. application Ser. No. 08/233,251, filed Apr. 26, 1994, in the names of Harley White and Joseph Bocek, for "SELECTIVE CARDIAC ACTIVITY ANALYSIS ATRIAL FIBRILLATION DETECTION SYSTEM AND METHOD AND ATRIAL DEFIBRILLATOR UTILIZING SAME", and/or copending U.S. application Ser. No. 08/278,055, filed Jul. 20, 1994, in the names Jaeho Kim and Harley White, for "SYSTEM AND METHOD FOR REDUCING FALSE POSITIVES IN ATRIAL FIBRILLATION DETECTION", which applications are assigned to the assignee of the present invention and incorporated herein by reference.

When cardioversion is required, the microprocessor 66, under software control pursuant to operating instructions obtained from the memory 80, implements the charge and delivery control 74. The charge and delivery control 74 first causes the charger of circuit 75 to charge the storage capacitor therein to a selected peak voltage. The charge and delivery control 74 monitors the charging of the capacitor. When the charge delivery control 74 determines that the voltage across the storage capacitor has reached a selected peak voltage, the microprocessor, through the charge and delivery control 74, terminates the charging.

After the charging of the storage capacitor is completed, the microprocessor implements a safety protocol 72. This confirms that R waves are being reliably sensed and detects for a cardiac interval which is longer than a preselected minimum time interval, as fully described in U.S. Pat. No. 5,207,219, which issued on May 4, 1993, for "ATRIAL DEFIBRILLATOR AND METHOD FOR PROVIDING INTERVAL TIMING PRIOR TO CARDIOVERSION", which is assigned to the assignee of the present invention and incorporated herein by reference.

Upon the successful completion of the safety protocol, the charge and delivery control 74 causes a discharge circuit 77, which is coupled to the storage capacitor of circuit 75, to discharge a portion of the energy stored in the storage capacitor. The discharged energy is applied to electrodes 44 and 46 of the intravascular lead 34 for applying the cardioverting electrical energy to the atria 16 and 18 of the heart 10.

Lastly, the atrial defibrillator 30 includes an RF transmitter/receiver 94 within enclosure 32. The RF transmitter/receiver includes a coiled antenna 96 for communicating through telemetry to an external programmer 100. The telemetry link provided by the RF transmitter/receiver 94 and the external programmer 100 permits the cardiologist to program the atrial defibrillator 30 with respect to its various programmable parameters and to enable the cardiologist to read from the atrial defibrillator 30 certain data which has been stored in the memory 80.

The entire cardioversion sequence, from original detection of an atrial fibrillation episode through successful cardioversion, is initiated at spaced apart predetermined times under the control of an activating means 83, including a wakeup timer 90 and a wakeup 81 of microprocessor 66. The predetermined time is preferably a programmable parameter of the atrial defibrillator 30 and provides wakeup of the atrial defibrillator 30 at spaced apart times for the detection and cardioversion of atrial fibrillation. As a result, the wakeup timer 90 may be reset after the completion of each therapy and after the completion of each atrial fibrillation detection which does not require intervention. As an example, atrial fibrillation detection may be initiated once every minute to once every twenty minutes.

Figure 2:
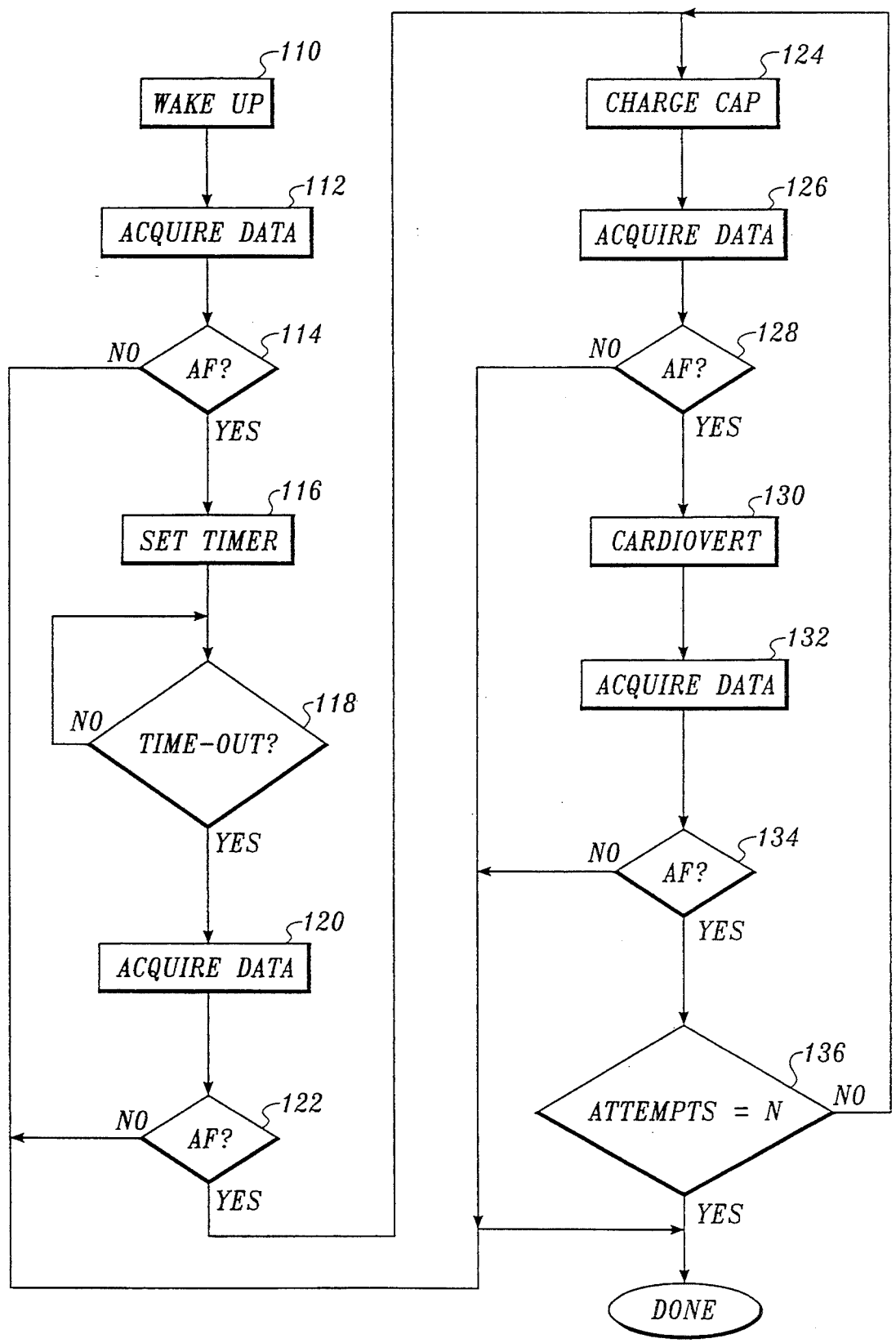
FIG. 2 is a flow diagram illustrating the manner in which the defibrillator of FIG. 1 may be implemented in accordance with a preferred embodiment of the present invention.

The manner in which the atrial defibrillator 30 detects an atrial fibrillation episode and cardioverts the atrial fibrillation episode in accordance with a preferred embodiment of the present invention will now be described with reference to FIG. 2.

The microprocessor 66 and hence the atrial fibrillation detector 70 are normally in a deactivated state along with sense amplifiers 50, 52, and 58, R wave detectors 54 and 56, multiplexer 64, analog-to-digital converter 60, direct memory access 68, and memory 80. As previously mentioned, when the wakeup timer 90 times a predetermined time interval, it causes the wakeup 81 of the atrial defibrillator 30 to initiate detection of a possible atrial fibrillation episode. When the atrial defibrillator 30 is to detect for an atrial fibrillation episode, the wakeup timer 90 first, in step 110, activates the wakeup 81 of the microprocessor 66, which then activates the sense amplifiers 50, 52, and 58, the analog-to-digital converter 60, the direct memory access 68 and the memory 80 to initiate an eight second acquisition period of step 112. During this acquisition period, the microprocessor 66 causes the multiplexer 64 to alternately couple the outputs of sense amplifiers 50 and 58 to the analog-to-digital converter 60 to permit the storing of digital samples of the electrograms sensed by electrodes 44 and 46 of lead 34 and electrodes 8 and 40 of lead 36. The electrogram digital samples for the entire eight seconds are stored in the process memory portion 88 of the memory 80.

When the eight second acquisition is completed, the microprocessor 66 implements the atrial fibrillation detector 70, in accordance with step 114, by processing the data stored in the process memory portion 88 to detect for atrial fibrillation in accordance with an atrial fibrillation detection algorithm. If atrial fibrillation is not detected, the process returns with the wakeup 81 of the microprocessor deactivating the data acquisition means 48, resetting the wakeup timer 90, and then deactivating the microprocessor 66. The wakeup timer 90 then proceeds to time its predetermined time interval to once again activate the wakeup 81 of microprocessor 66 at the next time in which a possible atrial fibrillation episode is to be detected.

If atrial fibrillation is detected in step 114, the microprocessor sets and starts timer 76 in step 116 for timing a delay time period. As illustrated by step 118, the timer 76 is repeatedly interrogated for time-out, and no further action is taken until the timer 76 does time-out. During the time in which the timer 76 performs its timing of the delay time period, the atria are being given an opportunity to spontaneously revert to normal sinus rhythm before therapy intervention is initiated. The delay time period may vary from patient to patient, depending upon each patient's medical history. However, and as an example, the delay time period may be as long as one hour or as short as five minutes.

As will be seen shortly, if the atria should spontaneously revert to normal sinus rhythm during the delay time period, therapy intervention is not performed. This avoids the patient receiving the application of the cardioverting electrical energy to the atria for this episode and conserves the energy of the battery 92.

After the timer 76 times-out, another data acquisition is performed in step 120, and the atrial fibrillation detector 70 thereafter again determines if the atria are in fibrillation in step 122, as previously described. If atrial fibrillation is not detected at this time, the process returns as previously described. As a result, the application of cardioverting electrical energy is withheld because the atria spontaneously reverted to normal sinus rhythm during the delay time period, rendering cardioversion unnecessary.

Although not illustrated, before the process returns, an additional step may be performed in logging the uncardioverted episode in an episode log in memory 80 for later retrieval by the cardiologist. Further steps may also be contemplated, such as storing in memory 80 the electrogram digital samples utilized by the atrial fibrillation detector 70 in determining that the atria had returned to normal sinus rhythm.

If atrial fibrillation is detected in step 122 by the atrial fibrillation detector 70, the charge delivery control 74 causes the charge and storage capacitor circuit 75 to charge the storage capacitor to a preselected peak voltage in step 124. When the capacitor is charged, another data acquisition is performed in step 126 and the atrial fibrillation detector 70, in step 128, once again determines if the atria 16 and 18 of the heart 10 are still in fibrillation.

If the atrial fibrillation detector 70 determines that the atria are not still in fibrillation, the process is completed and the wakeup 81 deactivates the data acquisition means 48, resets the wakeup timer 90, and then deactivates the microprocessor 66, as previously described.

The wakeup timer 90 then proceeds to time its predetermined time interval.

If the atria are still in fibrillation, the microprocessor 66 then applies cardioverting electrical energy to the atria in step 130 by first implementing the safety protocol 72, as previously described. When the safety protocol is completed, the charge delivery control 74 causes the discharge circuit 77 to discharge a portion of the energy stored in the storage capacitor of circuit 75 between electrodes 44 and 46 for cardioverting the atria of the heart.

Following the delivery of the cardioverting electrical energy to the atria, in step 130, another eight second data acquisition is performed in step 132. The atrial fibrillation detector 70 then, in step 134, once again determines if the atria are in atrial fibrillation. If the atria are not in fibrillation and thus have been successfully cardioverted, the process returns with the wakeup 81 deactivating the data acquisition means 48, resetting the wakeup timer 90, and then deactivating the microprocessor 66. The wakeup timer 90 then proceeds to time its predetermined time interval and will once again initiate the detection of a possible atrial fibrillation episode at the next predetermined time.

If, in step 134, it is determined that the heart is still in atrial fibrillation, the microprocessor then, in step 136, determines if the atria, for this fibrillation episode, have been provided with cardioverting electrical energy a predetermined number of times (N). If the atria have been provided with cardioverting electrical energy a predetermined number of times without successfully cardioverting the atria, the process is considered completed and returns. If, however, additional cardioversion attempts remain, the atrial defibrillator 30 will recharge the capacitor of circuit 75 in the same manner as previously described and the cardioversion sequence is repeated, but preferably at a higher energy level.

As a result of the foregoing, the atrial defibrillator of the present invention delays therapy intervention after initial fibrillation detection by a delay time period to provide the atria with an opportunity to spontaneously revert to normal sinus rhythm. As a result, unnecessary cardioverting attempts may be avoided. This not only reduces potential patient discomfort, but also serves to potentially reduce power consumption of the implanted defibrillator battery.

While a particular embodiment of the present invention has been shown and described, modifications may be made. For example, the present invention may also be employed to advantage in defibrillators which continuously monitor heart activity for possible fibrillation. Such a defibrillator is described, for example, in U.S. Pat. No. 5,282,837, which issued on Feb. 1, 1994, for "ATRIAL DEFIBRILLATOR AND METHOD", which patent is also assigned to the assignee of the present invention and incorporated herein by reference.

It is therefore intended in the appended claims to cover all such changes and modifications which fall within the true spirit and scope of the invention.

What is claimed is:

1. An implantable atrial defibrillator for applying cardioverting electrical energy to the atria of a human heart in need of cardioversion, said atrial defibrillator comprising:

sensing means for sensing electrical activity of the heart;

atrial fibrillation detecting means responsive to said sensed electrical activity of the heart for detecting if the heart is in atrial fibrillation and providing a first detect signal upon detecting atrial fibrillation;

timing means for timing a delay time period responsive to said first detect signal and providing a time-out signal upon timing said delay time period;

said atrial fibrillation detection means being further responsive to said time-out signal for redetecting for atrial fibrillation of the heart and providing a second detect signal upon redetecting atrial fibrillation; and, cardioverting means responsive to said second detect signal provided by said atrial fibrillation detecting means for applying cardioverting electrical energy to the atria of the heart.

2. An atrial defibrillator as defined in claim 1 wherein said atrial fibrillation detecting means is normally in a deactivated state and wherein said defibrillator further includes activating means for activating said atrial fibrillation detecting means at spaced apart predetermined times.

3. An atrial defibrillator as defined in claim 2 wherein said activating means includes second timing means for timing a predetermined time interval.

4. An atrial defibrillator as defined in claim 3 wherein said second timing means times said predetermined time interval responsive to said atrial fibrillation detecting means failing to determine that the heart is in atrial fibrillation.

5. An atrial defibrillator as defined in claim 3 wherein said second timing means times said predetermined time interval responsive to said cardioverting means cardioverting the atria of the heart.

6. A method of applying cardioverting electrical energy to the atria of a human heart in need of cardioversion, the method including the steps of:

sensing electrical activity of the heart;

detecting if the heart is in atrial fibrillation in response to the sensed electrical activity;

timing a delay time period upon detecting atrial fibrillation of the heart;

redetecting for atrial fibrillation of the heart after the delay time period is completed and responsive to said sensed electrical activity; and, applying cardioverting electrical energy to the atria upon redetecting atrial fibrillation of the heart.

7. A method as defined in claim 6 wherein said detecting step is performed at predetermined spaced apart times.

* * * * *